(12) United States Patent
Christou et al.

(10) Patent No.: US 7,311,982 B2
(45) Date of Patent: Dec. 25, 2007

(54) LUMINESCENT POLYMERS

(75) Inventors: Victor Christou, Oxford (GB); Annette Steudel, Oxford (GB)

(73) Assignee: ISIS Innovation Limited, Oxford (GB)

( * ) Notice: Subject to any disclaimer, the term of this patent is extended or adjusted under 35 U.S.C. 154(b) by 307 days.

(21) Appl. No.: 10/469,205

(22) PCT Filed: Feb. 26, 2002

(86) PCT No.: PCT/GB02/00821

§ 371 (c)(1),
(2), (4) Date: Jan. 5, 2004

(87) PCT Pub. No.: WO02/068560

PCT Pub. Date: Sep. 6, 2002

(65) Prior Publication Data

US 2004/0113124 A1 Jun. 17, 2004

(30) Foreign Application Priority Data

Feb. 26, 2001 (GB) .................................. 0104700.0

(51) Int. Cl.
*H01L 51/50* (2006.01)
*C09K 11/06* (2006.01)
(52) U.S. Cl. .............. 428/690; 428/917; 313/504; 313/506; 252/301.16; 427/66
(58) Field of Classification Search ................ 428/690, 428/917; 313/504, 506; 252/301.16; 427/66
See application file for complete search history.

(56) References Cited

U.S. PATENT DOCUMENTS

| 5,442,021 A | 8/1995 | Heiliger ................ 526/241 |
| 5,922,481 A | 7/1999 | Etzbach et al. .......... 428/690 |
| 6,869,693 B2 | 3/2005 | Fryd et al. ............. 428/690 |
| 7,060,372 B2 | 6/2006 | Fryd et al. ............. 428/690 |

FOREIGN PATENT DOCUMENTS

| EP | 579 151 A2 | 1/1994 |
| EP | 579 151 A3 | 1/1994 |
| GB | 1 448 655 | 9/1976 |
| JP | 1973-15628 | 2/1973 |
| JP | 1975-91572 | 7/1975 |
| JP | 2-52072 | 2/1990 |
| JP | 1993-210273 | 8/1993 |
| JP | 1995-101441 | 4/1995 |
| JP | 7-252475 | 10/1995 |
| JP | 1997-131083 | 5/1997 |
| JP | 1999-55905 | 3/1999 |
| JP | 1999-69281 | 3/1999 |
| JP | 2000-252072 | * 9/2000 |
| JP | 2000-268890 | 9/2000 |

OTHER PUBLICATIONS

Journal of the American Chemical Society, 1998, 120, p. 6781-6784.*
Thin Solid Films, 331, (1998), p. 158-164.*
Journal of the American Chemical Society, (2001), 123, p. 9436-9442.*
"Chelation", IUPAC Compendium of Chemcial Technology, 2nd Edition, 1997, 1 page.
International Search Report in PCT/GB02/00821 dated May 31, 2002.
International Preliminary Examination Report in PCT/GB02/00821 dated Oct. 1, 2002.
"Preparation and Copolymerization of Divalent Metal Salts of Ethylene Glycol-Methacrylate-phthalate", Matsuda et al., J. Appl. Polym. Sci. 17(6), 1973.
"Preparation and Copolymerization of Polyvalent Metal Salts of Ethylene Glycol-Methacrylate-Phthalate", Matsuda et al., J. Appl. Polym. Sci. 17(7), 1973.
"Ab Initio and DFT Study on Electronic Structures and Photoelectric Properties of Tris-8-Hydroxyquinoline Aluminum", Su et al., Gaodeng Xuexiao Huaxue Xuebao 21(9), 2000.
"Synthesis of Polymerizable Organometallic Derivs. of N-Vinylamide of Phthalic Acid and N-(p,o-carboxyphenyl)acrylyl(methacrylyl)amides", Kiseleva et al.
Search Report in GB 0104700.0 dated Aug. 31, 2001.

* cited by examiner

*Primary Examiner*—Dawn Garrett
(74) *Attorney, Agent, or Firm*—Marshall, Gerstein & Borun LLP

(57) ABSTRACT

A monomer which luminesces in the visible region upon excitation is described of the formula: $M^{n+} (L)^{n-} (CL)_x$ in which n+ is the valency of M, (L) represents one or more anionic ligands with a total valency of n such that at least one of the ligands possesses the formula: Ch-X—Y wherein Ch represents a chelating group which is a ligand fragment comprising the chelate binding sites and the part of the rest of the ligand with which the binding sites are conjugated, Y represents an olefinic group and X represents a spacer comprising a chain of at least 4 carbon and/or hetero atoms, x is 0, 1, or 2, CL represents a neutral co-ligand and M represents a metal atom of group 2, 12, 13, d-block or f-block with the proviso that if Y is part of a styrene or substituted styrene group then M is a f-block or d-block metal.

32 Claims, 4 Drawing Sheets

LUMINESCENT POLYMERS

CROSS-REFERENCE TO RELATED APPLICATION

This is the U.S. national phase of International Application No. PCT/GB02/00821 filed Feb. 26, 2002, the entire disclosure of which is, incorporated herein by reference.

BACKGROUND OF THE INVENTION

1. Field of the Invention

This invention relates to organometallic-based luminescent polymers.

2. Description of Related Technology

Luminescent metal complexes incorporated into a polymeric structure should have significantly improved EL properties, because diffusion of ions and crystallization of the luminescent layer are hindered by the polymeric phosphor. This leads to a far higher stability of the device structure. Furthermore, this new type of metal monomer complex can be easily patterned by imagewise exposure to actinic radiation (UV light, visible light, electron beams, or X-rays).

In general, there are four different groups of metal ion containing polymers:

(1) Coordination polymers and poly(electrolytes),
(2) Polymers containing neutral polar groups doped with metal complexes,
(3) Polymer-metal-complexes, prepared by deprotonation of the polymer and subsequent reaction with metal salts, and
(4) Metal-polymer complexes, prepared by polymerisation of the metal monomer complex Most of these groups have significant disadvantages, which hinder application in EL devices. Thus coordination polymers tend to be insoluble in organic solvents due to their salt-like structure. Doping of polymers, e.g. epoxy resin with lanthanide diketonates, poly(propylene oxide) with lanthanide halides, poly(ethylene glycol) with metal nitrates, or polymer based crown ethers with Eu(II) salts, gives undefined mixtures with poor metal co-ordination environments, leading to poor luminescence properties. Another drawback is the electronically insulating character of this type of polymer, which makes charge injection very difficult. The largest group of metal-polymer-complexes consists of polymers containing acidic or β-diketonate groups, which are easily deprotonated to form strong ionic bonds with the lanthanide or aluminium ion. Well known complexes include carboxylic acid homo- and co-polymers, e.g. poly (styrene acrylic acid), poly(dicarboxylic acid styrene), poly (diketonate), and poly(arylene ether) containing 8-hydroxyquinoline in the side chain as well as doped poly(pyridine). The main disadvantage here is that usually only low doping levels can be achieved (generally 10 wt % at maximum).

To avoid this major drawback, the fourth approach has been used. Metal complexes have been prepared from ligands that contain polymerisable groups, e.g. acrylate. Polymerisation of the monomeric metal complex gives a polymer with a defined structure. These types of compounds have the potential to possess excellent properties in EL devices, combining the advantages of polymers with the emission characteristics of the chosen organometallic complex, for example the colour purity of lanthanide emission. Examples of this class of polymer are poly(lanthanide methacrylate) and poly(lanthanide octanoate), but these are not luminescent. Heteroleptic acrylate complexes with photo-sensitising ligands, e.g. β-diketonate, salicylate, and naphthoate, and their copolymerisation with methylmethacrylate and styrene have been reported. An EL device using this type of material was highly inefficient.

However the use of such luminescent lanthanide acrylate monomers gives rise to disadvantages. In particular homopolymerisation is impossible due to steric hindrance. Therefore the lanthanide monomers have been copolymerised with methylmethacrylate or styrene. This gives an insulating polymer with a low lanthanide content. Other disadvantages include the very low solubility of acrylate complexes in non-coordinating solvents and the very high toxicity of acrylic acid and similar monomers with high vapour pressure.

GENERAL DESCRIPTION

Accordingly there is a need for luminescent polymers derived from monomers where these disadvantages are reduced or eliminated. According to the present invention there is provided a monomer of the formula:

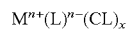

$$M^{n+}(L)^{n-}(CL)_x$$

in which n+ is the valency of M, (L) represents one or more anionic ligands with a total valency of n− such that at least one of the ligands possesses the formula:

$$Ch\text{-}X\text{—}Y$$

wherein Ch represents a chelating/ion-binding group which is a ligand fragment comprising the chelate binding sites and the part of the rest of the ligand with which the chelate binding sites are conjugated, Y represents an olefinic group and X represents a spacer or linker comprising a chain, of at least 4 carbon and/or hetero atoms, x is 0, 1 or 2, CL represents a neutral co-ligand and M represents a metal atom of group 2, 12, 13, d-block or f-block with the proviso that if Y is part of a styrene or substituted styrene group then M is a f-block or d-block metal, said monomer being one which emits visible light upon excitation i.e. it luminesces in the visible region.

A definition of chelation can be found in IUPAC Compendium of Chemical Technology, 2nd Ed. 1997.

Such monomers possess significant advantages over those proposed hitherto. In particular homo polymerisation of the novel metal monomers is made possible because of the presence of the spacer between the chelating/ion-binding and the olefinic groups of the ligand. Also solution-processing of these monomers is generally very easy, because they are highly soluble in a wide range of non-coordinating organic solvents and show excellent film-forming properties, particularly when bulky organic groups are present in the monomer. The olefinic group can be polymerised by actinic radiation. Imagewise exposure of the monomer film can thus give an insoluble patterned polymer film which will emit visible light upon excitation. This facilitates the production of patterned multi-colour EL displays which can have long lifetimes. Further the toxicity of the olefinic ligand is significantly lower due to the lower volatility of these compounds.

The central ion is a metal atom of group 2, 12, 13, d-block or f-block of the Periodic Table (see Inorganic Chemistry, Striver Atkins, Langford, OUP, 1990). Preferred metals include beryllium, aluminium, zinc, iridium, platinum, rhodium, osmium, ruthenium, europium, samarium, terbium, yttrium, dysprosium, cerium and gadolinium. In this connection, it will be appreciated that although the ions are generally trivalent, it is possible for the monomer to possess a divalent ion such as $Be^{2+}$, $Zn^{2+}$ and $Eu^{2+}$ or a tetravalent atom such as $Ce^{4+}$.

The key feature in the monomers of the present invention is that they possess at least one ligand of formula Ch-X—Y. As indicated, the presence of the spacer X enables one to obtain homo polymers while the group Y enables polymerisation to take place.

The nature of the chelating group, Ch, is not particularly critical and the known binding groups for metal ions can form part of the chelating group including, carboxylic acid, dicarboxylic acid, hydroxy carboxylic acid, a β-diketonate or indeed a Schiff base-type ligand including acyl phenols and iminoacyl groups. A preferred chelating group is a carboxylic acid group. In case of M being a metal of group 2, 12 or 13, or d-block, the metal chelating group can be hydroxyquinoline or a derivative, such as methacrylic acid-2-(8-hydroxyquinol-5-ylmethoxy) ethyl ester, Schiff bases and derivatives; some additional metal binding groups that can form part of the chelating group are β-diketonate, carboxylic acid, alkoxide, amide, imide, aryl and aryloxide. If M is a d-block metal other metal chelating groups include 2-phenyl pyridine and derivatives, 2-pyridyl thiophene and derivatives, or 7,8-benzoquinoline and derivatives. The derivatives are typically the corresponding compounds substituted by conventional electron withdrawing or donating groups such as alkyl, halo, haloalkyl and alkyloxy. It is to be appreciated that the group Ch includes, in addition to the binding sites, for example a carboxylic acid group the surrounding atoms into which the binding sites are conjugated. Thus Ch is, for example,

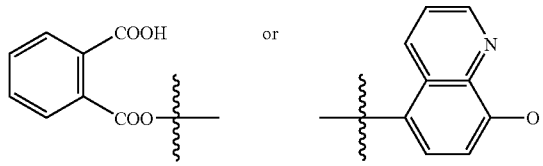

and not simply —COO or —COOH. This is important in calculating the number of atoms in the spacer; none of the atoms in the phthalate group shown form part of the spacer. As indicated, the spacer comprises a chain of at least four carbon and/or hetero atoms. This represents the number of atoms between the olefinic double bond of the olefinic group, Y, and the chelating group. Typically, the spacer will contain 4 to 30 atoms, more generally 4 to 20, preferably 6 to 16, more preferably 6 to 12, and especially 6 to 10 atoms. Generally, the chain will comprise carbon atoms and, optionally, oxygen atoms although the presence of other hetero atoms including nitrogen, sulphur and phosphorus is not excluded. Thus the spacer can be derived from, for example, a diol or a diamine, eg. ethylenediamine, or can be an alkyl/aryl chain. As indicated in more detail below, the spacer can also possess one or more donor groups capable of coordinating to M.

The olefinic group Y is typically part of an acrylic compound, for example acrylate, methacrylate, acrylonitrile, methacrylonitrile, acrylamide and methacrylamide. Also useful are vinyl esters of monocarboxylic and polycarboxylic acids, N-vinyllactams such as N-vinylpyrrolidone, and vinyl ethers of monohydroxy and polyhydroxy compounds; allyl compounds, for example allyl esters of monocarboxylic and polycarboxylic acids, and allyl ethers of monohydroxy or polyhydroxy compounds as well as allyl cyclic ethers. Vinyl aromatic compounds such as styrene, vinylnaphthalene or N-vinylcarbazole may not be suitable if polymerisation of the luminescent monomer is to be photo-initiated. Styrene, for example, has a very low triplet energy level, ~463 nm, (Handbook of Photochemistry, New York, 1973) comparable to the triplet energy of the visible light activated initiators used to activate the luminescent monomers. Hence styrene quenches the visible activated initiators and cannot be effectively photopolymerised. Visible light activated initiators are preferable since the luminescent monomers absorb light in the UV region and the resulting polymerisation is incomplete and also UV light can damage the materials. For the lanthanide complexes, which absorb at shorter wavelengths, it may be possible to use an initiator with a higher triplet energy, which would then be compatible with styrene. However for the group 2, 12 and 13, styrene and other vinyl aromatic groups with low triplet energies are not appropriate. The group Y can be represented by the general formula:

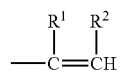

where $R^1$ and $R^2$, which may be the same or different, represents a hydrogen atom, or an alkyl group of 1 to 6 carbon atoms. It will be appreciated that with vinyl aromatic compounds, for example, the aromatic groups form part of the linker. In a preferred embodiment, Y comprises a methacrylate group. In this connection it should be pointed out that the carbonyl carbon atom represents the first member of the spacer chain X while the carboxylate oxygen atom represents the second member of the spacer chain.

As indicated in the general formula, the monomers of the present invention comprise one or more anionic ligands with a total valency of n– (so that the charge on the ion M is balanced). For the typical case of a metal 3+ ion this means that the total charge of the anionic ligands should be 3–. As indicated, one or more of the ligands Ch-X—Y can be present. Any ligand which is not Ch-X—Y can be any usual anionic ligand, preferably including oxygen or nitrogen donor systems, typically possessing an aromatic carboxylic acid, dicarboxylic acid, β-diketonate or hydroxy carboxylic acid or a Schiff base; specific examples include aromatic carboxylic acids such as isoquinoline carboxylic acid, 1-naphthoic acid and 4-tert-butylbenzoic acid. If M is a d-block metal any ligand which is not Ch-X—Y can also be a carbon nitrogen donor system such as 2-phenyl pyridine and derivatives. If all the L groups are the same then a homoleptic complex is formed. If at least one L group is different a heteroleptic complex is formed.

Preferably the monomer according to the present invention comprises an aromatic or heteroaromatic sensitizing group, more preferably the monomer according to the present invention comprises a phenyl sensitizing group.

If M is an f-block, in particular a lanthanide, ion, a sensitizing group should be present in the ligand Ch-X—Y or, if it is not, in another ligand L. As is well known, suitable sensitizing ligands have a triplet energy higher than the first excited state of the lanthanide atom and the emission colour is determined by the choice of the lanthanide metal. In the case of M being a main group or d-block metal, a ligand based fragment that emits visible light or enables charge transfer based light emission from the complex should be present in the ligand Ch-X—Y or in another ligand L. The band-gap of the emitting centre should be large enough to provide luminescence at a wavelength no longer than 750 nm so that it is in the visible region. One of skill in the art will be able to tailor the molecule accordingly. For example if the band gap of the compound is too wide an electron donative functional group can be incorporated to reduce it. In general, though, the presence of electron donating groups results in a band gap which is too narrow. Suitable ligand based fragments or sensitising groups include substituted β-diketonates, Schiff bases, hydroxyphenol and derivatives, aromatic and heteroaromatic groups and their substituted derivatives such as benzene, naphthalene, benzophenone, quinoline, pyrrole, pyrazole, pyrazolone, porphyrine, furan, thiophene, indole and thionapthene. Specific examples of suitable sensitizing ligands include 1-napthoic acid and isoquinolinecarboxylic acid for europium and 4-tert-butyl-benzoic acid for terbium, hydroxyquinoline for aluminium and 2-phenylpyridine, 2-phenylbenzoxazole, 2-phenylbenzothiazole or 2-pyridylthianaphthene for iridium. In a preferred embodiment, the sensitizing group is present in the ligand Ch-X—Y, for example as part of the chelating group as in the group of the formula

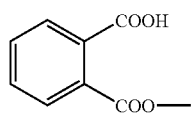

A particularly preferred ligand Ch-X—Y for lanthanide metals is one derived from mono-2-(methacryloyloxy) ethyl phthalate [H(MEP)] which has the formula:

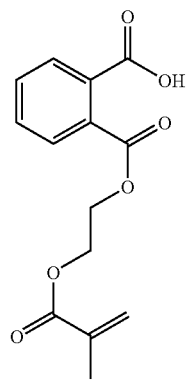

In this compound the chelating group Ch, is phthalate, Y is part of a methacrylate group while the linker X possesses a chain of 4 atoms, being carbon and oxygen atoms, more precisely 3 carbon atoms and 1 oxygen atoms with 1 of the carbon atoms being present as a carbonyl group. This ligand, H(MEP), is suitable for lanthanide metals, but is not appropriate for use with group 2, 12, 13 or d-block metals. The triplet level of HMEP is appropriately positioned so that it acts as a sensitising ligand for Eu or Tb, resulting in a luminescent lanthanide complex. However the band-gap is too large for HMEP to form a luminescent complex with group 2, 12, 13 or d-block metals.

The monomers of the present invention can also include one or two neutral co-ligands to prevent water or other solvent molecules coordinating to the metal ion. The usual co-ligands can be used for this purpose. Such neutral co-ligands can fill the coordination sphere around the central M ion, which is particularly relevant when M is a lanthanide, because the lanthanide ions tend to have a higher coordination number than group 2, 12, 13 or d-block metal ions. An appropriate co-ligand can also sensitise the lanthanide ion and can improve the solubility of the monomer. The co-ligand can be monodentate or bidentate. Suitable co-ligands include 1,10-phenanthroline and its derivatives, 2,2'-bipyridyl and its derivatives, dimethoxyethane, ethyleneglycols, phosphine oxides, ethylene diamines along with amines containing 1 or 2 donor atoms. If the anionic ligand does not act as a sensitiser then a co-ligand which possesses a sensitiser should be present. Sensitising co-ligands include 1,10-phenanthroline, 2,2'-bipyridyl, pyridine N-oxide, bathophenanthroline, and benzophenones and derivatives thereof. It is also possible to saturate the coordination sphere of the metal ion by additional donor groups, which are part of the anionic ligand (and can be part of the linker).

If M is a trivalent lanthanide ion then emission will be from the metal, and the choice of metal will dictate the emission colour. Otherwise the emission colour will depend on the choice of ligands (L) as well as the choice of metal. When the metal, M, is a group 2, 12 or 13 metal such as beryllium, zinc or aluminium, or a light d-block metal, then the complex will fluoresce. In a preferred example for Al, the Ch-X—Y ligand contains 8-hydroxyquinoline as the Ch group, where the spacer X comprises a chain of 6 atoms, more precisely 4 carbon atoms and 2 oxygen atoms with one of the carbon atoms being present as a carbonyl group. Thus a preferred monomer of this type possesses the formula:

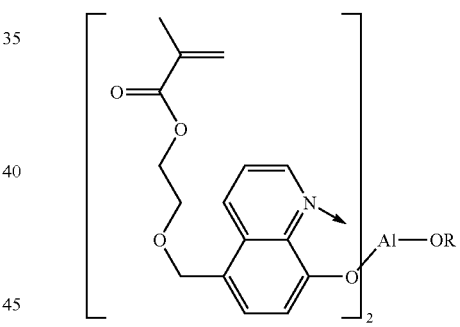

where OR is a ligand that binds to the aluminium, and can be a third methacrylic acid-2-(8-hydroxyquinolin-5-yl-methoxy) ethyl ester ligand, or an alternative ligand such as 2,4,6-triphenylphenolato or 2,4,6-2-naphtholato or other known suitable examples such as those disclosed in U.S. Pat. No. 5,141,671. When the metal, M, is a heavy d-block metal such as iridium, rhodium, osmium, platinum or ruthenium, spin orbit coupling gives rise to phosphorescence (radiative emission from triplet states). As is known, such complexes are capable of producing phosphorescent emission in organic light emitting devices (OLED), which can have clear efficiency benefits. In principle in an OLED three times as many triplet excitons are formed as singlet excitons. Both lanthanide complexes and other heavy metal phosphorescent emitters can harvest the triplet excitons and transfer them to a state that emits radiatively, whereas with fluorescent compounds only singlet excitons can decay radiatively, the remaining energy is lost in non-radiative processes. In a preferred example for heavy d-block metals, the Ch-X—Y ligand comprises a β-diketonate Ch group and there are two additional phenyl-pyridine anionic ligands. Thus a preferred ion of this type possesses the formula:

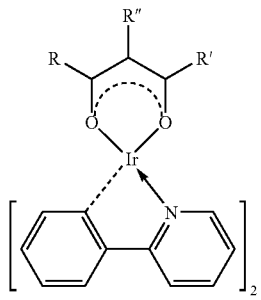

where one of R, R' and R" corresponds to X—Y and the other substituents include hydrogen, alkyl of 1 to 6 carbon atoms, halogen, haloalkyl, phenyl and thionyl.

The metal-containing monomers can be prepared by standard methods, known to those familiar with the art. The monomers of this invention can be generally be prepared by deprotonating a compound of the formula Ch-X—Y, and optionally any other anionic ligand compound, and reacting the deprotonated compound or compounds with a salt of the ion M, optionally in the presence of one or two neutral ligand compounds. The monomers are typically prepared by dissolving a compound of the formula Ch-X—Y in ethanol or other water soluble solvent. Ch-X—Y is then deprotonated eg. the ligand carboxylic acid is converted to $COO^-$. This can be achieved using a metal salt such as a carbonate, nitrate, halide, such as a chloride, or carboxylate such as an acetate. Typical metals include sodium and potassium. It is desirable that if a carboxylate is used it is a weaker acid than that of the ligand; if not, then excess ligand should be employed. In general, about equimolar quantities of the ligand-containing compound and the deprotonator should be used. If any other anionic ligands are employed these should be treated in the same way and then any neutral co-ligands incorporated. The metal ion is then added, typically dropwise. The lanthanide or other metal ion is generally provided in the form of a water soluble salt, typically a halide such as a chloride. The reaction generally proceeds but gentle warming may be necessary. The desired product can then be isolated, for example, by addition of water to precipitate it out of the solvent and then filtered. The complexes can also be prepared using anhydrous organic solvents and the techniques familiar to those skilled in the art.

As indicated, the monomers of the present invention can readily be converted into polymers. These polymers possess recurring units of the formula:

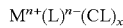

where M, CL, n and x are as defined above and (L) represents one or more anionic ligands with a total valency of n– such that at least one of the ligands possesses the formula:

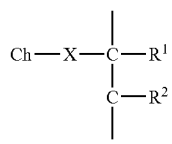

in which Ch and X are as defined above and $R^1$ and $R^2$, which may be the same or different, represent a hydrogen atom, or an alkyl group of 1 to 6 carbon atoms, preferably 1 or 2 carbon atoms. Preferably $R^2$ represents hydrogen and $R^1$ represents methyl.

The polymers of the present invention can be homo polymers or they can be derived from one or more olefinic comonomers including monofunctional monomers, for example N-vinylcarbazole and acrylate monomers of the type discussed above in relation to (L), and optional di-, tri- and tetrafunctional monomers. It will be appreciated that the polymer backbone will typically be non-conducting.

It is a particular advantage of the present invention that the polymers can be obtained readily by radical initiation giving rise to insoluble, preferably crosslinked, polymeric material. A crosslinked polymer with generally be produced if more than one ligand of the type Ch-X—Y is present in the monomer. The monomer layer can also be polymerised thermally or, particularly preferably by means of actinic radiation including UV light, visible light, electron beams, and X-rays. Typically, polymerisation of the monomer (or monomers), can take place in situ. In other words, a solution of the monomer(s) can be cast where the polymer is desired in an LED and then polymerised. In the case of irradiation-induced polymerisation, the layers can be structured by imagewise exposure. Systems which are based on crosslinking and can be photostructured are known in industry, for example in relation to printing plates and photoresists (see, for example, U.S. Pat. No. 5,922,481).

First, a suitable substrate is coated with the monomer solution. Examples of suitable substrates are glasses and films which are provided with a conducting coating and, further, optional hole injecting and hole transporting materials. An appropriate solution of a non-coordinating solvent containing the metal-containing monomer in addition to further, optional, components, such as comonomers, crosslinking agents and thermal initiators or photoinitiators, is applied to a substrate by spin- or dip-coating, by means of a knife coater or printing, and polymerised, preferably by means of actinic radiation. It is preferred that the photo polymerisation takes place in the absence of oxygen, for example in an nitrogen atmosphere. In case of imagewise exposure unexposed areas can be removed by washing out with a solvent for the monomer. Depending on the planned structure further layers can be deposited by spin- or knife-coating or by vapour deposition without risking intermixing of the layers.

In a preferred embodiment a solution of the monomer is spuncast to provide a layer of polymer which is typically 20 to 500, for example 50 to 100, nm thick. The monomer should desirably be dissolved in a non-coordinating solvent with a relatively high boiling point so that it evaporates slowly and thus gives rise to good quality film. Typically, the solvent is one possessing a boiling point from 70 to 150° C. including chloroform, xylene, toluene and halobenzenes, especially chlorobenzenes such as orthodichlorobenzene. Clearly, the concentration used will depend on the nature of the solvent and on the speed at which the solution is spun. Typically, though, the concentration will be from 5 to 100 mg per ml. Other methods including dip-coating and printing can, of course, also be used.

The polymers of the present invention are useful as forming a light emitting layer in a light emitting device. In its simplest form, an organic light emitting or electroluminescent device can be formed from a light emitting layer sandwiched between two electrodes, at least one of which must be transparent to the emitted light. Such a device can have a conventional arrangement comprising a transparent substrate layer, a transparent electrode layer, a light emitting layer and a back electrode. For this purpose the standard materials can be used. Thus, typically, the transparent substrate layer is typically made of glass although other transparent materials such as PET, acrylic resins and polyamides such as nylon can also be used.

The transparent electrode which typically forms the anode is preferably made from indium tin oxide (ITO) although other similar materials including indium oxide/tin oxide, tin oxide/antimony and zinc oxide/aluminum can also be used. Conducting polymers such as PANI (polyaniline) can also be used.

The back electrode is normally made of a low work function metal or alloy such as Al, Ca, Mg, Li, or MgAg. As is well known, other layers may also be present, including a hole transporting material and/or an electron transporting material. In an alternative configuration, the substrate may be an opaque material such as silicon and the light is emitted through the opposing electrode.

A particular advantage of the present invention resides in the fact that the layer of polymer of the invention can be incorporated in situ. Typically, therefore, a solution of the monomer is applied over the transparent electrode layer and then polymerised and any unpolymerised material removed, before the other layer or layers are applied. The polymerised material is typically insoluble, which allows further solutions to be deposited on top without disrupting the polymer layer. As is known in the art, a hole transporting material, such as PEDOT/PSS, may optionally be present between the transparent anode and the emissive layer.

Figure 1:
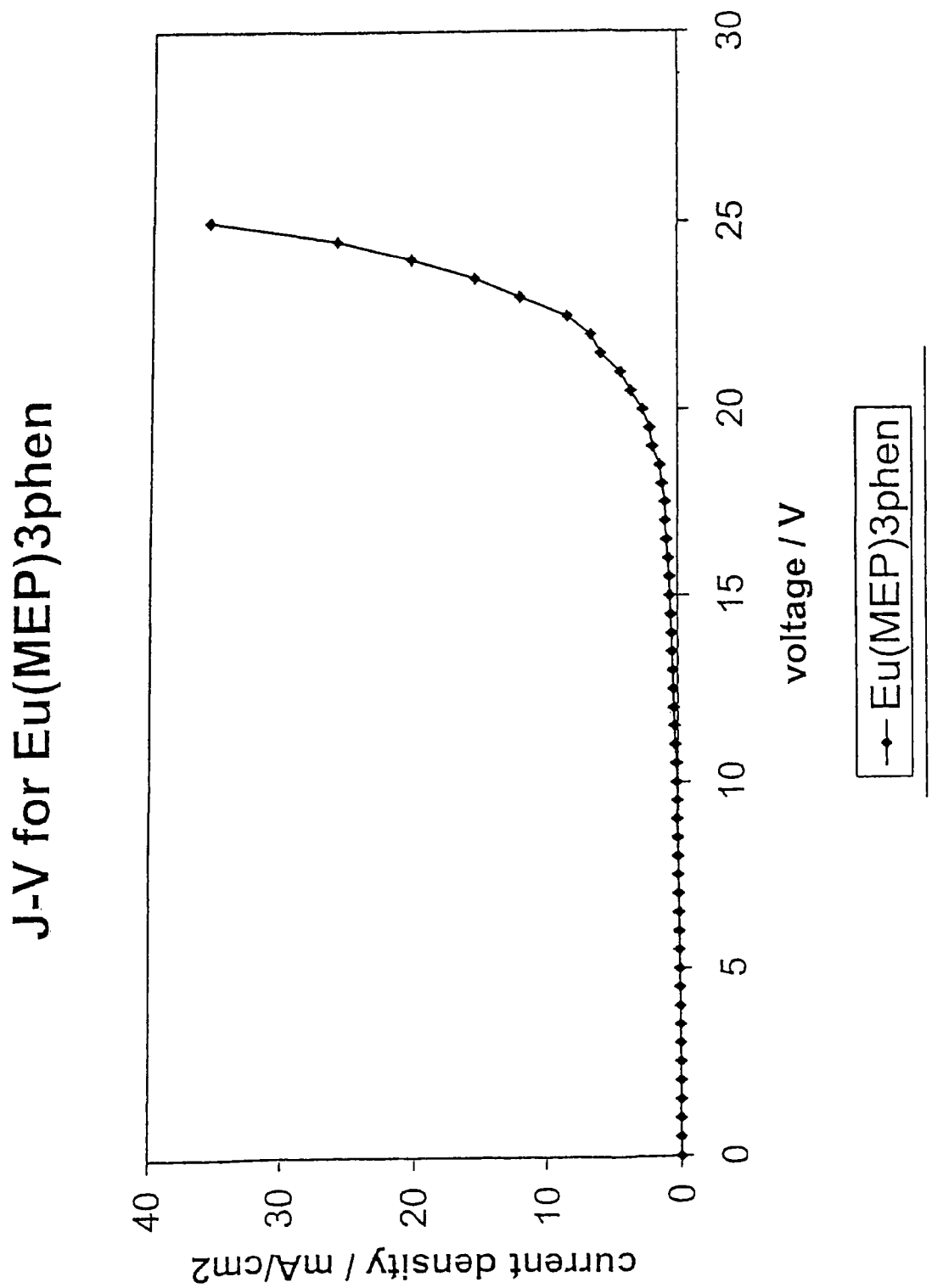
FIG. 1 shows a plot of voltage against current density for the organic light-emitting diode of Example 17.

The following Examples further illustrate the present invention.

EXAMPLE 1

Synthesis of [Eu(MEP)$_3$ bath]

4.57 g (16.4 mmol) mono-2-(Methacryloyloxy)ethyl phthalate (MEP) in 200 ml ethanol was reacted with 870 mg (8.2 mmol) Na$_2$CO$_3$ in 10 ml H$_2$O. Then 2.2 g (1.2 equivalents, 6.6 mmol) Bathophenanthroline (bath) was dissolved in this reaction mixture and 2 g (5.5 mmol) EuCl$_3$×6H$_2$O in 10 ml H$_2$O was added dropwise. The mixture was gently warmed until clear and then filtered. The product was precipitated from the filtered solution by drop-wise addition of 180 ml H$_2$O. The reaction mixture was stirred for 30 min. After filtration the precipitate was washed with 200 ml ethanol/H$_2$O 20:80 and 50 ml H$_2$O and dried overnight in vacuo to give 5.6 g (77% yield) colourless solid.

$C_{66}H_{59}EuN_2O_{18}$: expected/found: C 60.05/60.16, H 4.5/4.52, N 2.1/2.3, Eu 11.51/11.81. Photoluminescence: excitation: $\lambda_{max}$ 367 nm; emission: $\lambda_{max}$ 613+616 nm.

EXAMPLES 2–7

The same procedure was used to prepare the following compounds:

(2) [Eu(MEP)$_3$ phen] (phen=1,10-penanthroline) 5.0 g (78%) $C_{54}H_{47}EuN_2O_{18}$: expected/found: C 55.72/54.59, H 4.07/3.83, N 2.41/2.18. Photoluminescence: excitation: $\lambda_{max}$ 270+348 nm; emission: $\lambda_{max}$ 613+617+619 nm.

(3) [Sm(MEP)$_3$×H$_2$O] 1.29 g (57%) $C_{54}H_{47}N_2O_{18}Sm$: expected/found: C 50.44/50.44, H 4.13/4.19, Sm 15.04/15.44. No photoluminescence (4) [Tb(MEP)$_3$ phen] 980 mg (76%) $C_{54}H_{47}N_2O_{18}Tb$: expected/found: C 55.39/54.75, H 4.05/4.09, N 2.39/2.20. Photoluminescence: excitation: $\lambda_{max}$ 270+348 nm; emission: $\lambda_{max}$ 613+617+619 nm.

(5) [Y(MEP)$_3$ phen] 969 mg (75%) $C_{54}H_{47}N_2O_{18}Y$: expected/found: C 58.92/57.45, H 4.30/4.01, N 2.54/2.35. $^1$H-NMR (300 MHz, CDCl$_3$); 9.59 ppm (s, 2H), 8.09 (d, 2H), 7.67 (s, 2H), 7.48 (m, 5H), 7.08 (m, 9H), 5.8 (s, 3H), 3.82 (d, 12H), 1.75 (s, 9H). No photoluminescence.

(6) [Tb(MEP)$_3$ bipy] (bipy=2,2'-bipyridyl) 810 mg (50%) $C_{52}H_{58}N_2O_{18}Tb$ expected/found: C53.94' 52.56, H 5.05/5.08, N 2.42/2.21, Tb 13.72/14.04. Photoluminescence: excitation: $\lambda_{max}$ 287 nm; emission: $\lambda_{max}$ 543 nm.

(7) [Tb(MEP)$_3$ $^t$Bu-bipy] ($^t$Bu-bipy=4,4'-di-tert-butyl-2,2'-bipyridyl) 2.1 g (29%) $C_{60}H_{66}N_2O_{18}Tb$: expected/found: C 57.1/56.3, H 5.27/5.14, N 2.22/2.18, Tb 12.59/12.64. Photoluminescence: excitation: $\lambda_{max}$ 296+335 nm; emission: $\lambda_{max}$ 542 nm.

EXAMPLE 8

Synthesis of [Eu(MEP)(IQA)$_2$×H$_2$O]

1.25 g (4.5 mmol) mono-2-(Methacryloyloxy)ethyl phthalate and 1.56 g (9 mmol) Isoquinolinecarboxylic (IQA) acid were dissolved in 5 ml methanol and added to a solution of 1.13 g (13.5 mmol) NaHCO$_3$ in 3 ml methanol/H$_2$O 1:1 at 50° C. After 45 min stirring the solution was filtered and added drop-wise to a solution of 1.65 g (4.5 mmol) EuCl$_3$.6H$_2$O in 6 ml methanol. After stirring for 45 min at 50° C., all the volatiles were evaporated in vacuo and the product extracted with 30 ml CH$_2$Cl$_2$. After evaporation of the solvent in vacuo, the crude product was dissolved twice in THF and precipitated into hexane. The precipitate was dried in vacuo overnight to give 3.02 g (85% yield) of product as a colourless solid.

$C_{34}H_{27}EuN_2O_{11}$ expected/found: C 51.59/51.79, H 3.44/3.26, N 3.54/3.66, Eu 19.20/18.52. Photoluminescence (CH$_2$Cl$_2$): emission: $\lambda_{max}$ 615 nm, excitation: $\lambda_{max}$ 339 nm.

EXAMPLES 9–13

The same procedure was used to prepare the following compounds:

(9) [Sm(MEP)(IQA)$_2$×H$_2$O] 3.01 g (78%) $C_{34}H_{27}N_2O_{11}Sm$ expected/found: C 51.69/50.58, H 3.44/3.20, N 3.55/3.66, Sm 19.04/20.13. No photoluminescence.

(10) [Eu(MEP)(NA)$_2$×H$_2$O] (NA=1-naphthoic acid) 650 mg (58%) $C_{36}H_{29}EuO_{11}$ expected/found: C 54.76/55.12, H 3.70/3.73, Eu 19.25/19.07. Photoluminescence (CH$_2$Cl$_2$): emission: $\lambda_{max}$ 613 nm, excitation: $\lambda_{max}$ 251 nm.

(11) [Sm(MEP)(NA)$_2$×H$_2$O] 2.68 g (81%) $C_{36}H_{29}O_{11}Sm$ expected/found: C 54.87/55.19, H 3.71/3.88, Sm 19.09/19.15. No photoluminescence.

(12) [Tb(MEP)(TBA)$_2$] (TBA=4-tert-butylbenzoic acid) 1.62 g (41%) C$_{36}$H$_{39}$O$_{10}$Tb expected/found: C 54.69/55.26, H 4.97/5.48, Tb 20.10/20.12. Photoluminescence (CH$_2$Cl$_2$): emission: $\lambda_{max}$ 543 nm, excitation: $\lambda_{max}$ 253 nm.

(13) [Dy(MEP)(TBA)$_2$xH$_2$O] 1.0 g (27%) C$_{36}$H$_{39}$O$_{10}$Dy expected/found: C 53.24/53.04, H 5.09/5.01, Dy 20.01/21.12. No photouminescence.

EXAMPLE 14

Photopolymerisation of [Eu(MEP)$_3$ bath]

The photopolymerisation of [Eu(MEP)$_3$ bath] was initiated with 5 wt % diphenyl (2,4,6-trimethylbenzoyl) phosphine oxide. A solution of Europium monomer in toluene (30 mg/ml) was spin-cast on glass substrates. The glass substrates were then exposed to UV light in a nitrogen atmosphere. Patterning of the substrate was achieved by using a photo mask. After irradiation the monomer in the unexposed areas was removed by rinsing the substrate with toluene to give a 100 nm thick polymer film.

EXAMPLE 15

Red-Green Luminescent Substrate with [Tb(MEP)$_3$ bipy] and [Eu(MEP)$_3$ bath]

[Tb(MEP)$_3$ bipy] with 10 wt % 1-Hydroxycyclohexyl-phenyl ketone in CHCl$_3$ was spin-cast onto glass. After W exposure in nitrogen atmosphere through a photomask, unreacted monomer was washed off with CHCl$_3$. [Eu(MEP)$_3$ bath] with 10 wt % 1-Hydroxycyclohexyl-phenyl ketone was spun-cast from toluene solution. After irradiation through a photomask, unreacted monomer was removed with toluene.

EXAMPLE 16

Copolymerisation of [Eu(MEP)(IQA)$_2$xH$_2$O] with Methylmethacrylate MMA

In an argon atmosphere [Eu(MEP)(IQA)$_2$xH$_2$O] (5–30 wt %) was dissolved in inhibitor-free MMA. AIBN was added as a radical initiator. The sealed tube was placed in an oil bath at 60° C. After the reaction was complete (10–30 min), the product was dried for 30 min in vacuo to give colourless transparent plastic.

In a similar fashion [Eu(MEP)(IQA)$_2$xH$_2$O] was copolymerised with styrene and N-vinylcarbazole.

(1) Co-polymerisation of [Eu(MEP)(IQA)$_2$xH$_2$O] with MMA 5, 10, 30 wt %: Photoluminescence: max. emission: 615 nm, max. excitation: 374.

(2) Co-polymerisation of [Eu(MEP)(IQA)$_2$xH$_2$O] with styrene 10, 30, 50 wt %: Photoluminescence: max. emission: 614 nm, max excitation: 365 nm.

(3) Co-polymerisation of [Eu(MEP)(IQA)$_2$xH$_2$O] with N-Vinylcarbazole 1, 5, 10 wt %: Photoluminescence: max. emission: 615 nm, max. excitation: 390 nm.

EXAMPLE 17

Organic Light-Emitting Diode with [Eu(MEP)$_3$ phen]

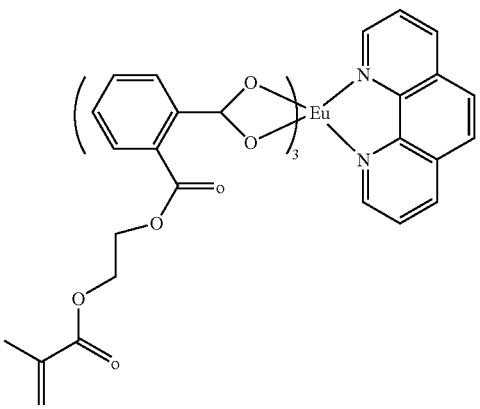

Organic light-emitting diodes fabricated by a combination of spin-coating and conventional evaporation were investigated with the organolanthanide compound shown above as the emissive material.

Patterned ITO substrates were pre-treated by sonication in detergent, 1:1 NH$_3$/H$_2$O$_2$, then deionised water followed by drying in an oven and O$_2$ plasma-treatment (65 W, 4 mins).

The typical working device structure was fabricated as follows;

The emissive layer consisting of 4–7 wt % [Eu(MEP)$_3$ phen], 47 wt % PBD (2,4-biphenylyl)-5-(4-tert-butylphenyl)-1,3,4-oxadiazole) in PVK (poly-(9-vinylcarbazole) (14 mg ml$^{-1}$ in CHCl$_3$) was deposited on the prepared ITO substrate by spin-coating (2000 rpm) a film approx. 80 nm thick. The film was dried on a hot plate in inert atmosphere (70° C.>2 h). Onto the spin-coated layer were evaporated (at 10$^{-6}$ mmHg and a deposition rate of 0.1 nm s$^{-1}$) metal contacts consisting of Ca (20 nm) overcoated by Al (100 nm).

FIG. 1 of the accompanying drawings gives a plot of voltage against current density.

Figure 2:
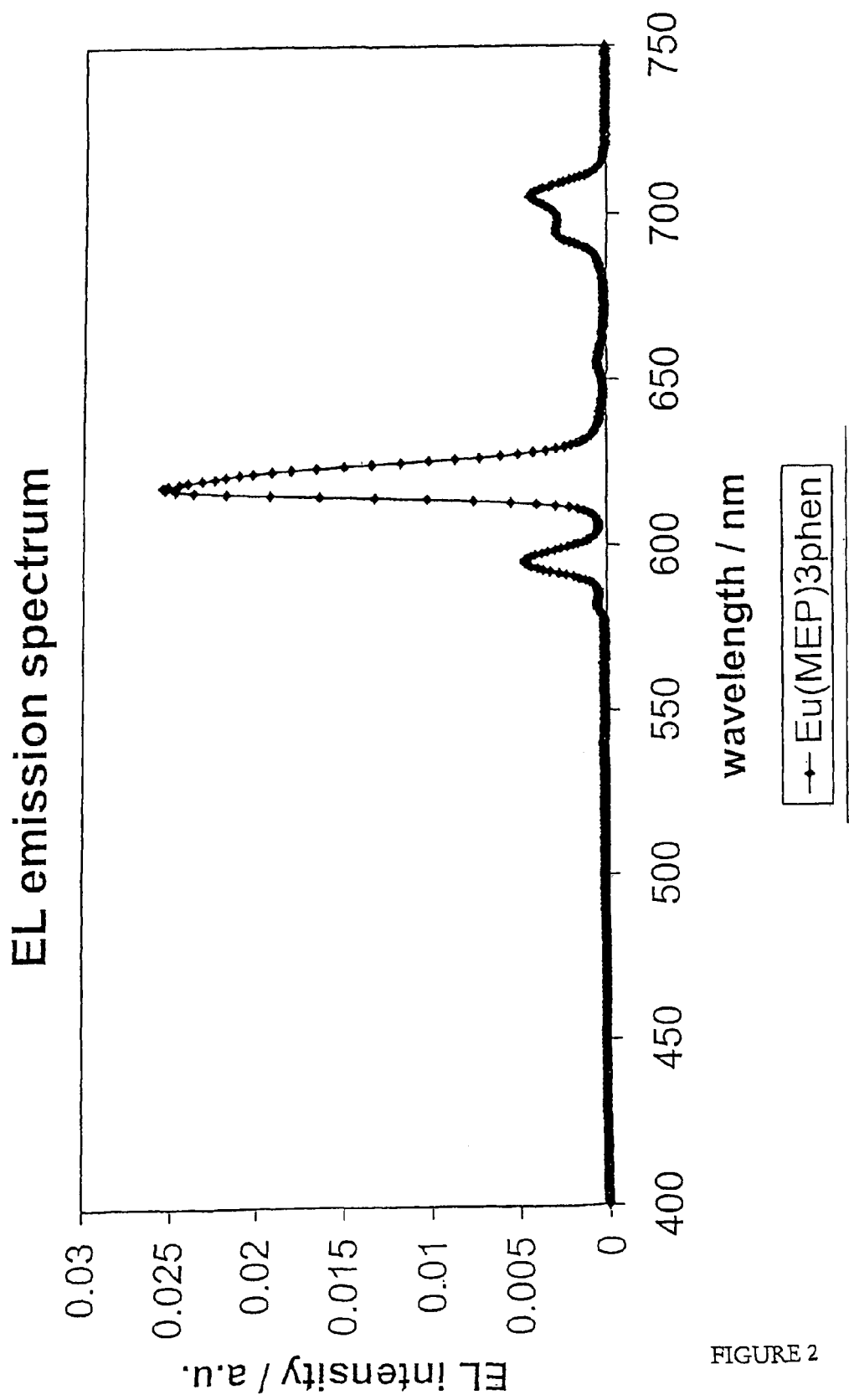
FIG. 2 shows an emission spectrum for the organic light-emitting diode of Example 17.

FIG. 2 gives the emission spectrum.

Current/Voltage, Brightness/Voltage analysis was performed using a Keithley 2400 Source meter programmed from an IBM compatible PC. Peak currents were of the order 40 mA cm$^{-2}$ (25 V) and peak brightness 1–2 cd m$^{-2}$ (25 V). The EL emission spectrum was measured using a ccd camera and gave an emission (max 615 nm) spectrum typical for that of europium ions.

EXAMPLE 18

Synthesis of Methacrylic Acid-2-(8-hydroxyquinolin-5-yl-methoxy) Ethyl Ester H(MAEQ)

A mixture of 5-chloromethyl-8-hydroxyquinoline hydrochloride (5.0 g, 21.7 mmol) and 2-hydroxyethyl methacrylate (20 ml, 143 mmol) was heated to 60° C. in vacuo for 2 days. After cooling to room temperature, H$_2$O (150 ml) was added and the solution made alkaline with dilute aqueous NH$_3$. The product precipitated and was collected on a filter, washed with dilute aqueous NH$_3$ and dried overnight in vacuo. This crude product was extracted into THF (250 ml) and filtered from undissolved residues. Evaporation of the THF in vacuo afforded a solid that was recrystallised twice from hexane to give colourless crystals of pure product as needles (4.9 g, 17 mmol, 79%).

Mp: 89° C. IR(film): 3055 cm$^{-1}$, 2955, 2857, 1713 (C=O), 1635 (C=C), 1581 (C=C$_{ring}$). $^1$H-NMR (δ, 300 MHz, DMSO-d$_6$): 8.86 ppm (m, 1H), 8.48 (m, 1H), 7.55 (dd, 1H, $^3$J=4.1, 8.5 Hz), 7.43 (d, 1H, $^3$J=7.8 Hz), 7.0 (d 1H, $^3$J=8.2 Hz), 5.95 (m, 1H), 5.64 (m, 1H), 4.84 (s, 2H), 4.23 (m, 2H), 3.69 (m, 2H), 1.83 (s, 3H). $^{13}$C {$^1$H}NMR (δ,300 MHz, DMSO-d$_6$): 166.3 ppm, 153.4, 147.8, 138.7, 135.6, 138.1, 128.5, 127.3, 125.6, 123.9, 121.6, 109.8, 69.9, 67.0, 63.5, 17.8. UV/Vis (CH$_2$Cl$_2$): 245 nm, 323.

EXAMPLE 19

Synthesis of Aluminium tris(methacrylic acid-2-(8-oxyquinolin-5-ylmethoxy) ethyl ester) Al(MAEQ)$_3$ At −80° C. in a nitrogen atmosphere trimethylaluminum (1.25 ml of a 2 M solution in toluene, 2.5 mmol) in dry toluene (125 ml) was added dropwise to methacrylic acid-2-(8-hydroxyquinoline-5-ylmethoxy) ethyl ester (2.15 g, 7.5 mmol) also in dry toluene (250 ml). The mixture was allowed to warm to −20° C. over 3 h at which point the reaction was quenched by addition of EtOH (3 ml) and left to warm to room temperature. After evaporation of solvent in vacuo, the residue was dissolved in toluene (250 ml), filtered through a pad of Celite and the volume reduced to ca. 10 ml. This toluene solution was then added dropwise to hexane (400 ml). After filtration the solid was dissolved in toluene (10 ml) and precipitated into hexane. This was repeated three times to give 1.54 g (69%) bright yellow solid.

C$_{48}$H$_{48}$AlN$_3$O$_{12}$: expected/found: C 65.08/63.68, H 5.46/5.32, N 4.74/4.81, Al 3.05/3.06. M.P.: no m.p., polymerisation starts at 60° C. IR (film): 2954 cm$^{-1}$, 2864, 1713 (C=O), 1636 (C=C), 1604 (C=C$_{ring}$), 1580 (C=C$_{ring}$). $^1$H-NMR (δ, 300 MHz, DMSO-d$_6$), 8.64 ppm (m, 6H), 7.49 (m, 6H), 6.75 (dd, 3H), 5.6 (m, 6H), 4.81 (m, 6H), 4.2 (m, 6H), 3.67 (m, 6H), 1.74 (m, 9H). FAB-MS: m/z=885 (20%, M+), 599 (100%). UV/Vis (CH$_2$Cl$_2$): 261 nm, 390. Photoluminescence (CH$_2$Cl$_2$): emission: λ$_{max}$ 534 nm, excitation: λ$_{max}$ 381 nm. Photoluminescence (powder): emission: λ$_{max}$ 532 nm, excitation: λ$_{max}$ 381 nm.

EXAMPLE 20

Organic Light-Emitting Diode with Al(MAEQ)$_3$

Patterned ITO substrates were pre-treated in the usual way by sonication in detergent and DI water followed by drying in an oven. A hole injecting/transport layer of PEDOT/PSS having a thickness of 40 nm was deposited over the ITO on the substrate by spin-coating. The film was dried on a hot plate at 120° C. for 20 min. The emissive/electron transporting layer consisting of Al(MAEQ)$_3$ having a thickness of 80 m was deposited by spin-coating from toluene (15 mg/ml). Over the emissive layer LiF having a thickness of 1.5 nm and an Al cathode having a thickness of 200 nm were deposited in vacuum.

Figure 3:
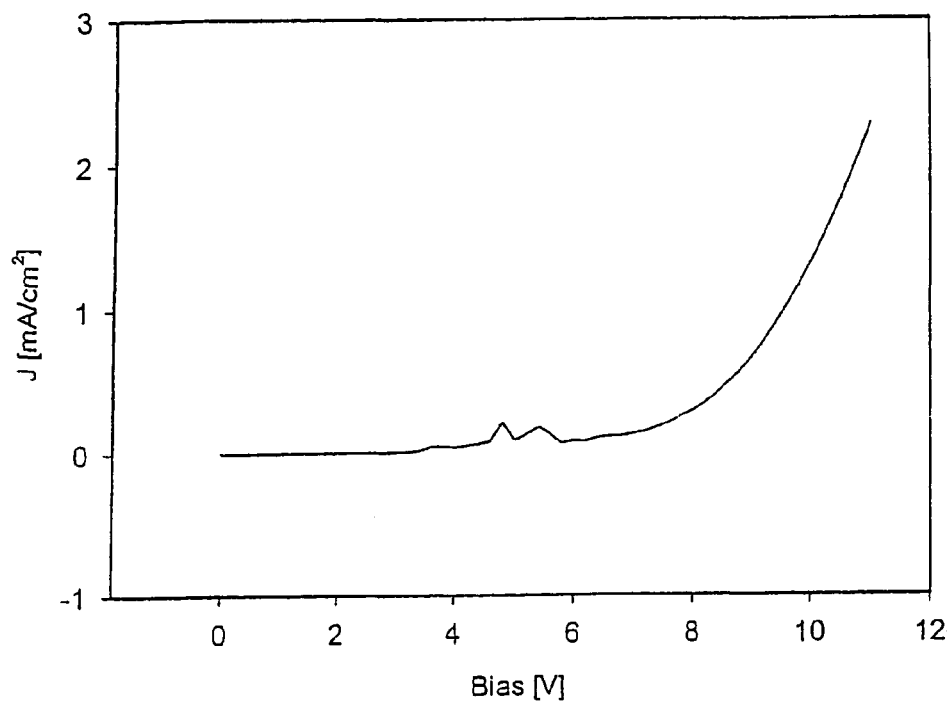
FIG. 3 shows a plot of voltage against current density for the organic light-emitting diode of Example 20.
Figure 4:
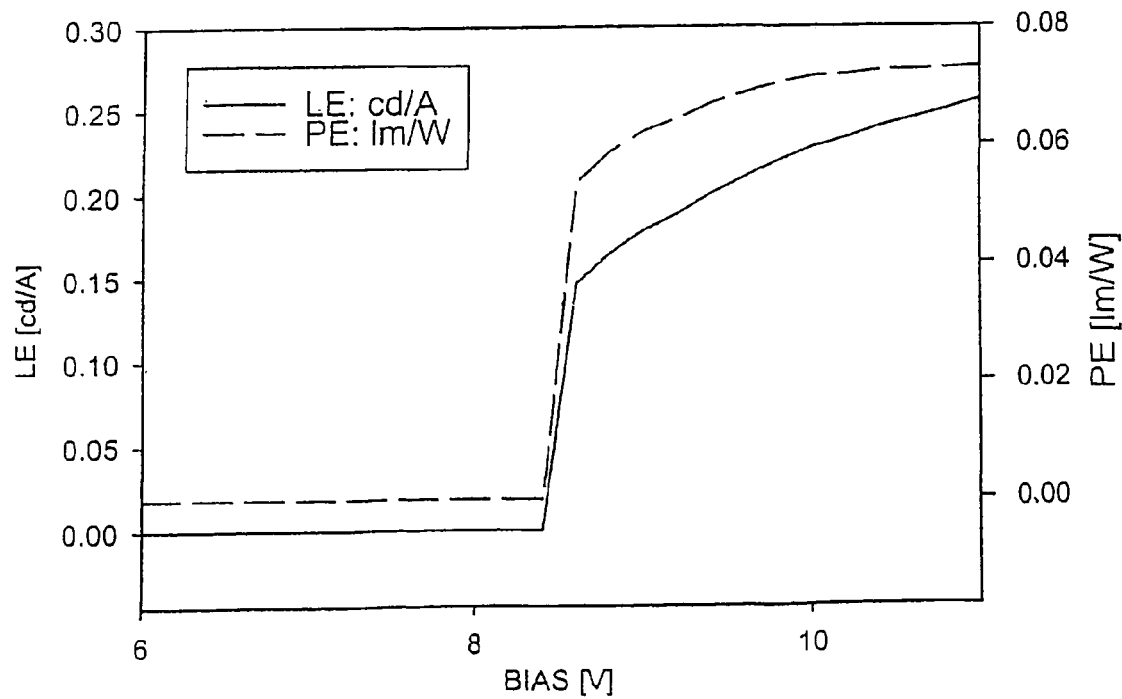
FIG. 4 shows efficiency-voltage characteristics for the organic light-emitting diode of Example 20; and, FIG. 5 shows emission spectra for the organic light-emitting diode of Example 20.
Figure 5:
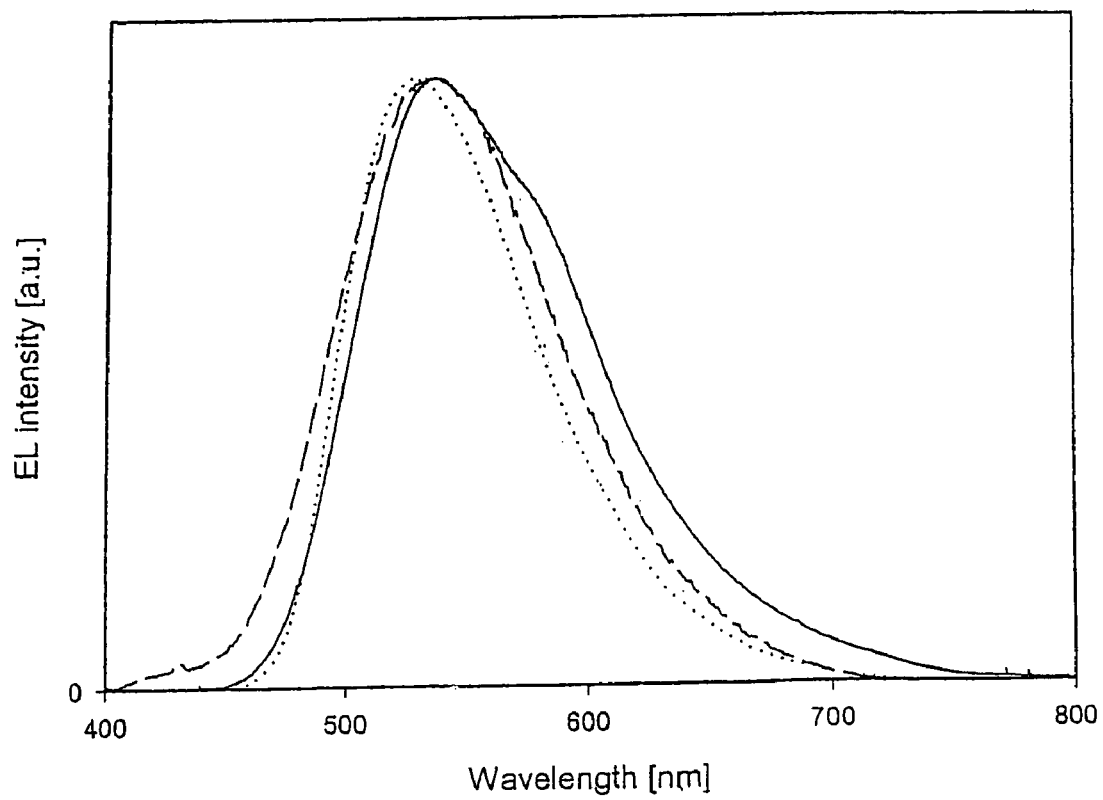

FIGS. 3 and 4 of the accompanying drawings gives the current-voltage (J-V) and efficiency-voltage characteristics of the device, respectively. A power efficiency of 0.07 lm/W and light efficiency of 0.25 Cd/A was achieved. The turn-on voltage was 8.5 V and at 11 V the brightness was 6 cd/m$^2$. FIG. 5 shows the following emission spectra: EL of the device (straight line), PL of Al(MAEQ)$_3$ in solution (CH$_2$Cl$_2$) (dashed line), and PL of Al(MAEQ)$_3$ in solid state (dotted line).

The invention claimed is:

1. A monomer which luminesces in the visible region upon excitation having the formula:

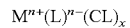

wherein n+ is the valency of M, (L) represents one or more anionic ligands with a total valency of n− such that at least one of the ligands possesses the formula

wherein Ch represents a chelating group which is a ligand fragment comprising the chelate binding sites and the part of the rest of the ligand with which the binding sites are conjugated, Y represents an olefinic group and X represents a spacer comprising a chain of at least four carbon and/or hetero atoms, x is 0, 1, or 2, CL represents a neutral co-ligand, and M represents a metal atom of group 2, 12, 13, or d-block with the proviso that if Y is part of a styrene or substituted styrene group then M is a d-block metal.

2. A monomer according to claim 1, wherein Ch is an oxygen or nitrogen donor system.

3. A monomer according to claim 1, wherein Ch is a carboxylic acid, dicarboxylic acid, hydroxycarboxylic acid, β-diketonate group or hydroxyquinoline group.

4. A monomer according to claim 1, wherein the spacer comprises 6 to 12 atoms.

5. A monomer according to claim 1, wherein the spacer comprises carbon atoms and, optionally, oxygen atoms.

6. A monomer according to claim 1, wherein the spacer comprises a donor or coordinating group.

7. A monomer according to claim 1, wherein Y is part of an acrylate or substituted acrylate group.

8. A monomer according to claim 7, wherein Y is part of a methacrylate group.

9. A monomer according to claim 1, wherein M is selected from the group consisting of europium, samarium, terbium, dysprosium, cerium, yttrium, and gadolinium.

10. A monomer according to claim 9, wherein (L) represents more than one anionic ligand, and at least one anionic ligand (L) does not possess the formula Ch-X-Y and comprises isoquinoline carboxylic acid, l-naphthoic acid, or 4-tert butylbenzoic acid.

11. A monomer according to claim 1, wherein M is selected from the group consisting of beryllium, zinc, aluminium, iridium, rhodium, osmium, platinum, and ruthenium.

12. A monomer according to claim 11, wherein (L) represents more than one anionic ligand, and at least one anionic ligand (L) does not possess the formula Ch-X-Y and comprises 8-hydroxyquinoline.

13. A monomer according to claim 1, wherein (L) represents more than one anionic ligand and at least one anionic ligand (L) does not possess the formula Ch-X-Y.

14. A monomer according to claim 13, wherein the anionic ligand (L) which does not possess the formula Ch-X-Y is phenyl pyridine.

15. A monomer according to claim 13, wherein the anionic ligand (L) which does not possess the formula Ch-X-Y is isoquinoline carboxylic acid, 1-naphthoic acid, or 4-tert butylbenzoic acid.

16. A monomer according to claim 13, wherein the anionic ligand(L) which does not possess the formula Ch-X-Y is 8-hydroxyquinoline.

17. A monomer according to claim 1, wherein x is 1 or 2.

18. A monomer according to claim 1, wherein Ch-X-Y has the formula:

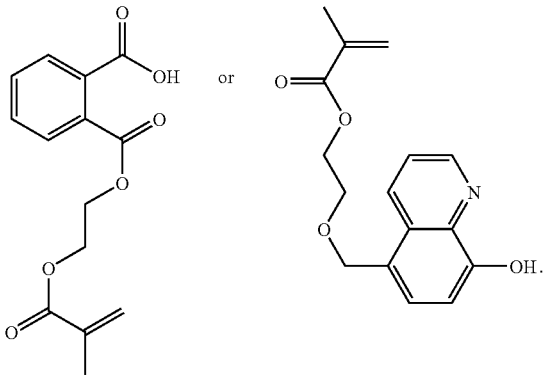

19. A monomer according to claim 1, wherein Y has the formula:

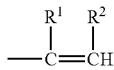

wherein R¹ and R², which are the same or different, represent a hydrogen atom, or an alkyl radical of 1 to 6 carbon atoms.

20. A process for making a light emitting device comprising:
subjecting a monomer to radical initiation so as to polymerize the monomer to form a polymer, said monomer having the formula:

$$M^+(L)^{n-}(CL)_x$$

wherein n+ is the valency of M, (L) represents one or more anionic ligands with a total valency of n− such that at least one of the ligands possesses the formula Ch-X—Y wherein Ch represents a chelating group which is a ligand fragment comprising the chelate binding sites and the part of the rest of the ligand with which the binding sites are conjugated, Y represents an olefinic group and X represents a spacer comprising a chain of at least 4 four carbon and/or hetero atoms, x is 0, 1, or 2, CL represents a neutral co-ligand, and M represents a metal atom of group 2, 12, 13, d-block or f-block with the proviso that if Y is part of a styrene or substituted styrene group then M is a f-block or d-block metal.

21. A process according to claim 20 comprising achieving radical initiation with UV light or visible light, and a photo initiator.

22. A process according to claim 20, comprising carrying out polymerization *in situ* where the polymer is desired.

23. A process according to 22, comprising spincasting a solution of the monomer to form a layer of the light emitting device and then polymerizing the monomer.

24. A process according to claim 23, comprising polymerizing using a photo mask, and removing unexposed portions using an organic solvent in which the monomer is soluble.

25. A process according to claim 20, further comprising coating a substrate with a solution containing the monomer prior to subjecting the monomer to radical initiation.

26. A process for making a light emitting device comprising:
subjecting a monomer to actinic radiation so as to polymerize the monomer to form a polymer, said monomer having the formula:

$$M^+(L)^{n-}(CL)_x$$

wherein n+ is the valency of M, (L) represents one or more anionic ligands with a total valency of n− such that at least one of the ligands possesses the formula Ch-X—Y wherein Ch represents a chelating group which is a ligand fragment comprising the chelate binding sites and the part of the rest of the ligand with which the binding sites are conjugated, Y represents an olefinic group and X represents a spacer comprising a chain of at least 4 four carbon and/or hetero atoms, x is 0, 1, or 2, CL represents a neutral co-ligand, and M represents a metal atom of group 2, 12, 13, d-block or f-block with the proviso that if Y is part of a styrene or substituted styrene group then M is a f-block or d-block metal.

27. A process according to claim 26, comprising carrying out polymerization *in situ* where the polymer is desired.

28. A process according to claim 27, comprising spincasting a solution of the monomer to form a layer of the light emitting device and then polymerizing the monomer.

29. A process according to claim 28, comprising polymerizing using a photo mask, and removing unexposed portions using an organic solvent in which the monomer is soluble.

30. A process according to claim 26, further comprising coating a substrate with a solution containing the monomer prior to subjecting the monomer to actinic radiation.

31. A light emitting device which comprises a layer of a polymer which possesses recurring units of the formula:

$$M^{n+}(L)^{n-}(CL)_x$$

wherein M represents a metal atom of group 2, 12, 13,d-block or f-block, n+ is the valency of M, CL represents a neutral co-ligand, x is 0, 1, or 2, and (L) represents one or more anionic ligands with a total valency of n−such that at least one of the ligands possesses the formula:

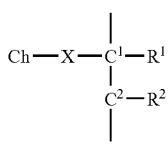

wherein Ch represents a chelating group which is a ligand fragment comprising the chelate binding sites and the part of the rest of the ligand with which the binding sites are conjugated, X represents a spacer comprising a chain of at least four carbon and/or hetero atoms, R¹ and R², which are the same or different, represent a hydrogen atom, or an alkyl radical of 1 to 6 carbon atoms, and C¹ and C² represent first and second carbon atoms.

32. A light emitting device according to claim 31, comprising a transparent substrate layer, a transparent electrode layer, a light emitting layer, and a back electrode, wherein the light emitting layer comprises said polymer.

* * * * *

UNITED STATES PATENT AND TRADEMARK OFFICE
CERTIFICATE OF CORRECTION

PATENT NO.        : 7,311,982 B2                                        Page 1 of 1
APPLICATION NO.   : 10/469205
DATED             : December 25, 2007
INVENTOR(S)       : Victor Christou et al.

It is certified that error appears in the above-identified patent and that said Letters Patent is hereby corrected as shown below:

At Column 15, line 35, "$M^+$" should be -- $M^{n+}$ --.

At Column 16, line 7, "$M^+$" should be -- $M^{n+}$ --.

Signed and Sealed this

Twenty-fourth Day of June, 2008

JON W. DUDAS
*Director of the United States Patent and Trademark Office*